(12) United States Patent
Oft

(10) Patent No.: US 8,822,405 B2
(45) Date of Patent: Sep. 2, 2014

(54) USES OF MAMMALIAN CYTOKINES AND AGONISTS; RELATED REAGENTS

(75) Inventor: Martin Oft, Palo Alto, CA (US)

(73) Assignee: Merck, Sharp & Dohme Corp., Rahway, NJ (US)

(*) Notice: Subject to any disclaimer, the term of this patent is extended or adjusted under 35 U.S.C. 154(b) by 589 days.

(21) Appl. No.: 12/548,784

(22) Filed: Aug. 27, 2009

(65) Prior Publication Data

US 2010/0015132 A1 Jan. 21, 2010

Related U.S. Application Data

(63) Continuation of application No. 10/893,562, filed on Jul. 16, 2004, now abandoned.

(60) Provisional application No. 60/488,263, filed on Jul. 18, 2003.

(51) Int. Cl.
*A61K 38/00* (2006.01)

(52) U.S. Cl.
USPC .......................................................... 514/1.1

(58) Field of Classification Search
CPC ... A61K 38/17; A61K 38/1793; A61K 38/19; A61K 38/20; C07K 14/435; C07K 14/52; C07K 14/54
See application file for complete search history.

(56) References Cited

U.S. PATENT DOCUMENTS

| | | | |
|---|---|---|---|
| 2002/0068323 | A1 | 6/2002 | Saris et al. |
| 2002/1146819 | | 10/2002 | Sims et al. |
| 2002/0173623 | A1 | 11/2002 | Reche-Gallardo et al. |
| 2003/0099947 | A1 | 5/2003 | Bazan et al. |
| 2003/0186875 | A1 | 10/2003 | De Waal Malefyt et al. |
| 2004/0022813 | A1 | 2/2004 | Bystryn |

FOREIGN PATENT DOCUMENTS

| | | |
|---|---|---|
| CN | 1 385 441 A | 12/2002 |
| WO | WO 00/17362 A1 | 3/2000 |
| WO | WO 02059260 A2 * | 8/2002 |
| WO | WO 02/068646 A2 | 9/2002 |
| WO | WO 03032898 A2 * | 4/2003 |
| WO | WO 03/065985 A2 | 8/2003 |

OTHER PUBLICATIONS

English Translation of Chinese Patent Application No. 1385441 submitted on Aug. 27, 2009 as references AG.
Waller et al., "Modulation on antitumor immune responses by hematopoietic cytokins . . ." Cancer, vol. 97, No. 7, pp. 1797-1809, 2003.
Yang et al., "Gentic Polymorphism and Tumor Immunotherapy", Current Pharmacogenomics, vol. 1, pp. 37-57, 2003.
Search Report for International Application No. PCT/US2004/022928, mailing date: Nov. 23, 2004.
Developmental Therapeutics Program NCI/NIh, Cell Lines in the In Vitro Screen [online], [retrieved Jan. 17, 2005], Retrieved from the Internet: <http://dtp.nci.nih.gov/docs/misc/common_files/cell_list.html>.
Gilliet, et al. (2003) *J. Exp. Med.* 197:1059-1063 "Human Dendritic Cells Activated by TSLP and CD40L Induce Proallergic Cytotoxic T Cells".
Luo, Y. et al., "Novel human lymphokine, its coding sequence and use for treating tumour", AN 2003-279588, XP-002301394, (Dec. 12, 2002) (1 page).
Monks, et al. (1991) *J. Natl. Cancer Inst.* 83:757-766 "Feasibility of a High-Flux Anticancer Drug Screen Using a Diverse Panel of Cultured Human Tumor Cell Lines".
Oft et al., (2002) *Nat. Cell Bio.* 4:487-494 "Metastasis is driven by sequential elevation of H-ras and Smad2 levels".
Pandey, et al. (2000) *Nat. Immunol.* 1:59-64 "Cloning of a receptor subunit required for signaling by thymic stromal lymphopoietin".
Park, et al. (2000) *J. Exp. Med.* 192:659-670 "Cloning of the Murine Thymic Stromal Lymphopoietin (TSLP) Receptor: Formation of a Functional Heteromeric Complex Requires Interleukin 7 Receptor".
Quentmeier et al., Cloning of human thymic stromal lymphopoietin (TSLP) and signaling mechanisms leading to proliferation. Leukemia. Aug. 2001;15(8):1286-92.
Reche, et al. (2001) *J. of Immunol.* 167:336-343 "Human Thymic Stromal Lymphotoietin Preferentially Stimulates Myeloid Cells".
Sims, et al. (2000) *J. Exp. Med.* 192:671-680 "Molecular Cloning and Biological Characterization of a Novel Murine Lymphoid Growth Factor".
Tonozuka, et al. (2001) *Cytogenet Cell Genet.* 93:23-25 "Molecular cloning of a human novel type 1 cytokine receptor related to δ1/TSLRP".
Bowie, et al. Science, vol. 247: 1306-1310, 1990.
Lazar, et al. Mol. Cell. Biol. 8(3): 1247-1252, 1988.
Burgess, et al. J. Cell Biol. 111:2129-2138, 1990.
Ngo et al., in "The Protein Folding Problem and Tediary Structure Prediction", 1994, Merz, et al. (ed.), Birkhauser, Boston, MA, pp. 433, and 492-495.
Skolnick et al., From genes to protein structure an function: novel applications of computational approaches in the genomic era, Trends in Biotech. 18: 34-39, 2000.
Jain, "Barriers to drug delivery in solid tumors", Sci. Am. 171(1): 58-65, 1994.
Gura, "Systems for identifying new drugs are often faulty", Science 278 (5340), 1041-1042, 1997.
MSNBC News Services, "Mixed results on new cancer drug", Nov. 2000.
Thomas et al., Nature Reviews Genetics, 2003, 4: 346-358.
Thompson, FDA Consumer Magazaine, Sep.-Oct. 2000, 19-24.
Crystal, R.G. Science, vol. 270, Oct. 1995, pp. 404-410.
Shah et al., Cancer Res. 2001, 61:5268-5274.
Quentmeier et al., Leukemia, 2000, 15: 1286-1292.

* cited by examiner

*Primary Examiner* — Hong Sang
(74) *Attorney, Agent, or Firm* — Sheela Mohan-Peterson

(57) ABSTRACT

The present invention relates generally to uses of TSLP in the treatment of cancer.

2 Claims, No Drawings

USES OF MAMMALIAN CYTOKINES AND AGONISTS; RELATED REAGENTS

This application is a continuation of U.S. application Ser. No. 10/893,562, filed Jul. 16, 2004, which claims the benefit of U.S. Provisional Patent Application No. 60/488,263, filed Jul. 18, 2003.

FIELD OF THE INVENTION

The present invention relates generally to uses of mammalian cytokine molecules and related reagents. More specifically, the invention relates to identification of mammalian cytokine-like proteins and inhibitors thereof that can be used in the treatment of cancer.

BACKGROUND OF THE INVENTION

Cancer is a progressive disease, occurring in a series of well-defined steps, usually as a consequence of activating or deactivating mutations. These mutations often render proliferating cells self-sufficient for growth, insensitive to growth-inhibitory signals, resistant to programs of terminal differentiation, senescence, or apoptosis, as well as endowing them with unlimited self-renewal capacity, the ability to orchestrate and direct sustained angiogenesis, and the ability to invade and thrive in ectopic tissue environments (see, e.g., Hanahan and Weinberg (2000) *Cell* 100:57-70).

The mammalian immune response is based on a series of complex cellular interactions, called the "immune network". Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions.

Lymphokines mediate cellular activities in a variety of ways. They have been shown to support the proliferation, growth, and differentiation of pluripotential hematopoietic stem cells into vast numbers of progenitors comprising diverse cellular lineages making up a complex immune system. Proper and balanced interactions between the cellular components are necessary for a healthy immune response.

Recently, a novel IL-7-like cytokine cloned from a murine thymic stromal cell line was identified as thymic stromal lymphoietin (TSLP) (see, e.g., J. E. Sims et al., (2000) *J. Exp. Med.* 192:671-680; U.S. Ser. No. 09/963,347, filed Sep. 24, 200; and SEQ ID NOs: 1, and 2). The activities of TSLP overlaps with those of IL-7; both stimulate thymocytes and mature T cells and facilitate B lymphopoiesis in cultures of fetal liver and bone marrow lymphocyte precursers. It has also been found that the receptor for TSLP is a heterodimer that consist of an IL-7-R-α chain and a common γ-like receptor chain (see, e.g., Reche et al., (2001) *J. of Immunol.* 167: 336-343; Y. Tonozuka et al., (2001) *Cytogenet Cell Genet.* 93:23-25; A. Pandey et al., (2000) *Nat. Immunol.* 1:59-64; L. S. Park et al., (2000) *J. Exp. Med.* 192:659-670; and SEQ ID NOs: 3, 4, 5, and 6).

Cancer development and metastasis is a multi-step process that involves local neoplasmic growth and invasion followed by dissemination to, and re-establishment at, distant sites. The neoplasm or tumor can consist of transformed cells and infiltration of stromal cells and cells of the immune system. The ability for a tumor to metastasize is the major determinant of cancer-patient mortality. TGF-β, has been implicated in both tumor suppression and progression (see e.g., Oft et al., (2002) *Nat. Cell Bio.* 4:487-494).

Many of the molecular and cellular mechanisms mediating the relationship between metastasis, innate immunity and cancer remain unsolved. TGF-β expression in tumors facilitates the formation of metastasis. The present invention suggests that TSLP is suppressed by TGF-β.

SUMMARY OF THE INVENTION

The present invention is based upon the discovery that the expression of the immune modulator, TSLP is reduced during tumor progression and addition of exogenous TSLP causes tumor regression.

The present invention provides a method of modulating a neoplasm comprising contacting the neoplasm with an effective amount of TSLP or an agonist thereof. The neoplasm is a tumor that is cancerous and epithelial derived that includes a breast tumor, colon tumor, lung tumor, ovarian tumor or a prostate tumor. In certain embodiments, the modulating is inhibition of tumor progression by tumor rejection. The tumor rejection can be tumor size reduction or loss of metastatic potential. In further embodiments, the neoplasm contains dendritic cells and the agonist may be a mutein of TSLP, a small molecule or an agonist antibody.

The present invention further provides a method of treating a subject suffering from a neoplasm comprising administering to the subject an effective amount of TSLP or an agonist thereof. The neoplasm is an epithelial derived cancerous tumor that may be a breast tumor, colon tumor, lung tumor, ovarian tumor, or a prostate tumor.

Also provided by the present invention is a method of preventing development of a neoplasm comprising a administration of an effective amount of TSLP or agonist thereof to a subject. The neoplasm is an epithelial derived cancerous tumor that may be a breast tumor, colon tumor, lung tumor, ovarian tumor, or a prostate tumor. In certain embodiments, TSLP or an agonist thereof may be administered as a vaccine adjuvant.

The present invention also provides a method of diagnosing a neoplasm comprising contacting a biological sample from a subject, with an TSLP or TLSPR antibody under conditions suitable for the formation of an antibody:antigen complex and detecting the complex.

DESCRIPTION OF THE DETAILED EMBODIMENTS

I. Definitions

The phrase "TSLP" refers to the nucleic and amino acids of SEQ ID NO: 1 and SEQ ID NO: 2. "TSLPR" is composed of two subunits, TSLPR and IL-7α, SEQ ID NOs: 4 and 6. The subunits are encoded by the nucleic acids of TSLPR and IL-7α, SEQ ID NOs: 3 and 5.

The phrase "effective amount" means an amount sufficient to ameliorate a symptom or sign of the medical condition. Typical mammalian hosts will include mice, rats, cats, dogs, and primates, including humans. An effective amount for a particular patient may vary depending on factors such as the condition being treated, the overall health of the patient, the method route and dose of administration and the severity of side affects. When in combination, an effective amount is in ratio to a combination of components and the effect is not limited to individual components alone.

An effective amount of therapeutic will decrease the symptoms typically by at least about 10%; usually by at least about 20%; preferably at least about 30%; or more preferably at least about 50%. The present invention provides reagents which will find use in therapeutic applications as described elsewhere herein, e.g., in the general description for treating disorders associated with the indications described above. Berkow (ed.) *The Merck Manual of Diagnosis and Therapy*, Merck & Co., Rahway, N.J.; Thorn, et al. *Harrison's Principles of Internal Medicine*, McGraw-Hill, NY; Gilman, et al. (eds.) (1990) *Goodman and Gilman's: The Pharmacological Bases of Therapeutics*, 8th Ed., Pergamon Press; *Remington's Pharmaceutical Sciences*, 17th ed. (1990), Mack Publishing Co., Easton, Pa.; Langer (1990) *Science* 249:1527-1533; *Merck Index*, Merck & Co., Rahway, N.J.; and Physician's Desk Reference (PDR); Cotran, et al. (eds), supra; and Dale and Federman (eds.) (2000) *Scientific American Medicine*, Healtheon/WebMD, New York.

The phrase "neoplasm" means an abnormal mass or colony of cells and/or infiltrating cells produced or attracted by a relatively autonomous new growth of tissue. Infiltrating cells can be dendritic cells, T cells and B cells. Most neoplasms arise from the clonal expansion of a single cell that has undergone neoplastic transformation. The transformation of a normal to a neoplastic cell can be caused by a chemical, physical, or biological agent (or event) that directly and irreversibly alters the cell genome. Neoplastic cells are characterized by the loss of some specialized functions and the acquisition of new biological properties, foremost, the property of relatively autonomous (uncontrolled) growth. Neoplastic cells pass on their heritable biological characteristics to progeny cells.

The past, present, and future predicted biological behavior, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm has a lesser degree of autonomy, is usually not invasive, does not metastasize, and generally produces no great harm if treated adequately.

The phrase "inhibition of tumor progression" refers to stopping tumor cell growth, invasion or metastasis depending on the state of the tumor. It should cover all the necessary steps of the evolution of a tumor including neovascularization and angiogenesis.

The phrase "metastatic potential or metastasis" refers to the process by which cancer spreads from one part of the body to another, the way it travels from the place at which it first arose as a primary tumor to distant locations in the body.

The extent to which metastasis occurs varies with the individual type of tumor. Melanoma, breast cancer, lung cancer, colon cancer, and prostate cancer are among the types of cancer that are prone to metastasize. When metastasis takes place, the metastases can form at a variety of sites in the body, with lymph nodes, lungs, liver, brain and bone marrow being the more common sites.

The phrase "mutein" or novel mutant proteins includes fragments, derivatives, and analogs of polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

The phrase "vaccine adjuvant" in the context of cancer, refers to a peptide used either alone or combined with different cytokines, non-specific stimulators, whole-cell tumors or antigen presenting cells such as dendritic cells (see e.g., Kochman et al, (1999) *Current Medical Research and Opinion*, 15:321-326 and Jager et al, (2002) *Current Opinion in Immunol.*, 14:178-182 and Mendelsohn et al; (2001) *The Molecular Basis of Cancer*, $2^{nd}$ Edition). The vaccine adjuvant may be administered for the prevention, amelioration, or treatment of tumors.

II. General

Thymic Stromal Lymphopoietin (TSLP) was originally discovered in the mouse and found to play a similar role as its homologue IL-7 in supporting early B and T cell development (see, e.g., J. E. Sims, supra; S. D. Levin et al., supra; and R. J. Ray, et al., supra). TSLP is a novel epithelial cell-derived cytokine, which induces dendritic cell (DC)-mediated $CD4^+$ and $CD8^+$ T cell responses. TSLP-activated CD $11c^+$ DCs potently activate and expand $CD8^+$ T cells, and induces their differentiation into interleukin (IL)-5 and IL-13-producing effectors exhibiting poor catalytic activity. Additional CD40L triggering of TSLP-activated DCs induced $CD8^+$ T cells with potent cytolytic activity, producing large amounts of interferon (IFN)-γ, while retaining their capacity to produce IL-5 and IL-13. TSLP has been found to play a role as an initiator of T cell responses and suggest that CD40L-expressing cells may act in combination with TSLP (see e.g., Gilliet, et al. (2003) *J. Exp. Med.* 197:1059-1063). The present invention is based on the surprising results that TSLP is a critical mediator in the development of neoplasms.

Recent studies analyzing TSLP suggest that it has potent effects on the ability of DCs to induce naïve CD8+ T cell activation and differentiation into IL-5 and IL-13 producing T cells (see e.g., Gilliet, et al. (2003) *J. Exp. Med.* 197:1059-1063). Activation of DCs appears to be a critical step in the pathogenesis of T cell mediated responses to tumors. The molecular mechanism underlying the signaling of DCs to induce T cell diseases is not clearly understood. The present findings that TSLP is highly expressed by a mouse squamous carcinoma cell line B9 suggest that TSLP represents a critical factor in understanding cancer. Studies in mouse models confirm the role that TSLP plays in tumor suppression.

Mouse squamous carcinoma cell line B9 and a derivative line, RS1, which carries overexpressed and activated Smad2 and H-ras, were studied for the mRNA expression level of the inflammatory cytokine, TSLP. It was observed that the B9 cell line expresses high levels of TSLP, whereas the RS1 cell line expresses strongly reduced levels of TSLP. Further studies were done by passing tumor cells into immune competent mice to observe the expression of TSLP.

Expression levels of TSLP were measured in various normal and tumor bearing tissues. TSLP expression was significantly higher in normal breast tissues when compared to proximal breast carcinoma tissues. Similar results were observed with normal colon, lung, ovarian, and prostate cancer tissues and proximal colon, lung, ovarian, and prostate cancer tissues. An interesting observation was that human tumor cells expressed significantly diminished amounts of TSLP when compared to the untransformed counterpart.

TSLP expression in carcinogen treated (DMBA, a site specific carcinogen, and TPA, a tumor promoter) mouse skin were initially elevated at 5 and 24 hour timepoints and subsequently fell to at or below control levels at later timepoints, again demonstrating that progression of the proliferative disorder coincides with a drop in TSLP expression.

It has been shown that TSLP and IL-7 engage similar signal transduction mechanisms. Both induce tyrosine phosphorylation of the transcription factor Stat5. While IL-7 mediated signaling occurs via activation of Janus kinases Jak1 and Jak 3; TSLP is unable to activate either enzyme, but may instead interact with Jak 2. It was further shown that the functional receptor for TSLP, TSLPR, when activated leads to phosphoralation of both Stat5 and Stat3 (see, e.g., Reche, et al. (2001) *J. Immunol.* 167:336-343).

In an in vivo model of tumor rejection, tumors induced in mice by Ep-ras cells were treated by a single administration of adenovirus containing mTSLP (Ad-TSLP) or by several administrations of mTSLP protein. In both cases, mTSLP appeared to significantly inhibit tumor growth when compared to control (Ad-GFP or PBS) treatment. This data indicates that TSLP exhibits potent tumor rejection activity probably caused by reactivation of the immune response to established tumors.

As noted above, inflammation appears to be a critical component of tumor progression, as many cancers arise in areas of infection, chronic irritation, and inflammation. The tumor microenvironment is an indispensable participant in the neoplastic process, fostering proliferation, survival and migration. This microenvironment appears to be largely orchestrated by inflammatory cells. The critical role of TSLP in the inflammatory process and endothelial growth factor activity, with the data presented above, one skilled in the art would recognize that the modulation of TSLP expression and activity is an important component in the progression of tumors.

The present invention provides methods and reagents to enhance the Th2 mediated response by agonizing the activities of TSLP. Enhancement of this response is useful in the treatment of disorders due to suppression of the immune system, e.g., cancer. Augmentation of dendritic cell activity induced by TSLP will be useful in the treatment of cancer. TSLP and/or agonists thereof will also be useful as a vaccine adjuvant.

II. Agonists and Antagonists

Agonists include the full-length cytokine protein, TSLP (see e.g., SEQ ID NO: 2). Peptides of those sequences, or variants thereof, will be used to induce receptor signaling. These variants include those that are conservatively substituted and with long half lives. Agonists can be modified to have longer half-lives by pegalation (PEG) or by tagging the agonist with the Fc portion of an IgG antibody (see e.g., Karmonos, (2001) BioDrugs, 15:705-711). Both methods provide a method to evade the immune response by not degrading as fast. For example, conjugation of the agonist with PEG significantly decreases the proteins clearance from plasma. Also contemplated are small molecules that also induce receptor signaling.

Antibodies can be raised to various epitopes of the TSLP proteins, including species, polymorphic, or allelic variants, and fragments thereof, both in their naturally occurring forms and in their recombinant forms. Additionally, antibodies can be raised to TSLPs in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective TSLPs, or screened for agonistic or antagonistic activity, e.g., mediated through a receptor.

A TSLP antibody can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying TSLP protein or its receptors (see, e.g., Chan (ed. 1987) *Immunology: A Practical Guide*, Academic Press, Orlando, Fla.; Price and Newman (eds. 1991) *Principles and Practice of Immunoassay*, Stockton Press, N.Y.; and Ngo (ed. 1988) *Nonisotopic Immunoassay*, Plenum Press, N.Y.). Cross absorptions, depletions, or other means will provide preparations of defined selectivity, e.g., unique or shared species specificities. These may be the basis for tests that will identify various groups of antigens.

Further, the antibodies, including antigen-binding fragments, of this invention can be potent antagonists that bind to the antigen and inhibit functional binding, e.g., to a receptor that may elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Immunoassays in the competitive binding format can be used for the crossreactivity determinations. The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying TSLP protein or its receptors (see, e.g., Chan (ed. 1987) *Immunology: A Practical Guide*, Academic Press, Orlando, Fla.; Price and Newman (eds. 1991) *Principles and Practice of Immunoassay*, Stockton Press, N.Y.; and Ngo (ed. 1988) *Nonisotopic Immunoassay*, Plenum Press, N.Y.). Cross absorptions, depletions, or other means will provide preparations of defined selectivity, e.g., unique or shared species specificities. These may be the basis for tests that will identify various groups of antigens.

Antibodies raised against each TSLP will also be useful to raise anti-idiotypic antibodies. These will be useful in detecting or diagnosing various immunological conditions related to expression of the respective antigens.

III. Therapeutic Compositions and Diagnostic Methods

Cytokines, such as IL-7, IL-12 or IL-23 antagonist and agonists thereof are normally administered parentally, preferably intravenously. Since such proteins or peptides may be immunogenic they are preferably administered slowly, either by a conventional IV administration set or from a subcutaneous depot, e.g. as taught by Tomasi, et al, U.S. Pat. No. 4,732,863. Means to minimize immunological reactions may be applied. Small molecule entities may be orally active.

Parenteral therapeutics may be administered in aqueous vehicles such as water, saline, or buffered vehicles with or without various additives and/or diluting agents. Alternatively, a vaccine adjuvant or, a suspension, such as a zinc suspension, can be prepared to include the peptide. Such a suspension can be useful for subcutaneous (SQ) or intramuscular (IM) injection (see, e.g., Avis, et al. (eds.)(1993) *Pharmaceutical Dosage Forms: Parenteral Medications* 2d ed., Dekker, NY; Lieberman, et al. (eds. 1990) *Pharmaceutical Dosage Forms: Tablets* 2d ed., Dekker, NY; Lieberman, et al. (eds. 1990) *Pharmaceutical Dosage Forms: Disperse Systems* Dekker, NY; Fodor, et al. (1991) *Science* 251:767-773, Coligan (ed.) *Current Protocols in Immunology*; Hood, et al.

*Immunology* Benjamin/Cummings; Paul (ed.) *Fundamental Immunology*; Academic Press; Parce, et al. (1989) *Science* 246:243-247; Owicki, et al. (1990) *Proc. Nat'l Acad. Sci. USA* 87:4007-4011; and Blundell and Johnson (1976) *Protein Crystallography*, Academic Press, New York.).

Selecting an administration regimen for a therapeutic depends on several factors, including the serum or tissue turnover rate of the entity, the level of symptoms, the immunogenicity of the entity, and the accessibility of the target cells, timing of administration, absorption through epithelial layers, etc. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of cytokine or small molecules is determined using standard methodologies.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Antibodies, antibody fragments, and proteins or polypeptides can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A preferred dose protocol is one involving the maximal dose or dose frequency that avoids significant undesirable side effects. A total weekly dose is generally at least 0.05 μg/kg body weight, more generally at least 0.2 μg/kg, most generally at least 0.5 μg/kg, typically at least 1 μg/kg, more typically at least 10 μg/kg, most typically at least 100 μg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg, see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (2003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

The present invention also provides for administration of biologics in combination with known therapies, e.g., steroids, particularly glucocorticoids, which alleviate the symptoms, e.g., associated with inflammation, or antibiotics or anti-infectives. Daily dosages for glucocorticoids will range from at least about 1 mg, generally at least about 2 mg, and preferably at least about 5 mg per day. Generally, the dosage will be less than about 100 mg, typically less than about 50 mg, preferably less than about 20 mg, and more preferably at least about 10 mg per day. In general, the ranges will be from at least about 1 mg to about 100 mg, preferably from about 2 mg to 50 mg per day. Suitable dose combinations with antibiotics, anti-infectives, or anti-inflammatories are also known.

Antibodies which specifically bind TSLP or TSLPR may be used for the diagnosis of conditions or diseases characterized by expression of TSLP or TSLPR, or in assays to monitor patients being treated with TSLP or TSLPR, agonists, antagonists or inhibitors. The antibodies useful for diagnostic purposes may be prepared in the same manner as those described above for therapeutics. Diagnostic assays for TSLP or TSLPR include methods that utilize the antibody and a label to detect TSLP or TSLPR in human body fluids or extracts of cells or tissues. The antibodies may be used with or without modification, and may be labeled by joining them, either covalently or non-covalently, with a reporter molecule. A wide variety of reporter molecules, which are known in the art, may be used, several of which are described above.

A variety of protocols including ELISA, RIA, and FACS for TSLP or TSLPR are known in the art and provide a basis for diagnosing altered or abnormal levels of TSLP or TSLPR expression. Normal or standard values for TSLP or TSLPR expression are established by combining body fluids or cell extracts taken from normal mammalian subjects, preferably human, with antibody to TSLP or TSLPR under conditions suitable for complex formation. The amount of standard complex formation may be quantified by various methods, but preferably by photometric, means. Quantities of TSLP or TSLPR expressed in subject, control and disease, samples from biopsied tissues are compared with the standard values. Deviation between standard and subject values establishes the parameters for diagnosing disease. The polynucleotides, which may be used, include oligonucleotide sequences, complementary RNA and DNA molecules, and PNAs. The polynucleotides may be used to detect and quantitate gene expression in biopsied tissues in which expression of TSLP or TSLPR may be correlated with disease. The diagnostic assay may be used to distinguish between absence, presence, and excess expression of TSLP or TSLPR, and to monitor regulation of TSLP or TSLPR levels during therapeutic intervention.

In one aspect, hybridization with PCR probes which are capable of detecting polynucleotide sequences, including genomic sequences, encoding TSLP or TSLPR or closely related molecules, may be used to identify nucleic acid sequences which encode TSLP or TSLPR. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding TSLP or TSLPR, alleles, or related sequences. Probes may also be used for the detection of related sequences, and should preferably contain at least 50% of the nucleotides from any of the TSLP or TSLPR encoding sequences. The hybridization probes of the subject invention may be DNA or RNA and derived from the nucleotide sequence of SEQ ID NO: 1 or from genomic sequence including promoter, enhancer elements, and introns of the naturally occurring TSLP or TSLPR.

Means for producing specific hybridization probes for DNAs encoding TSLP or TSLPR include the cloning of nucleic acid sequences TSLP or TSLPR or derivatives thereof into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Antibodies as well as polynucleotide sequences encoding TSLP or TSLPR may be used for the diagnosis of conditions or disorders which are associated with expression of TSLP or TSLPR. Examples of such conditions or disorders include carcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding TSLP or TSLPR may be used in Southern or northern analysis, dot blot, or other membrane-based technologies; in PCR technologies; or in dipstick, pin, ELISA assays or microarrays utilizing fluids or tissues from patient biopsies to detect TSLP or TSLPR expression. Such qualitative or quantitative methods are well known in the art.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

The broad scope of this invention is best understood with reference to the following examples, which are not intended to limit the inventions to the specific embodiments.

EXAMPLES

I. General Methods

Some of the standard methods are described or referenced, e.g., in Marniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1-3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Methods for protein purification include such methods as ammonium sulfate precipitation, column chromatography, electrophoresis, centrifugation, crystallization, and others (see, e.g., Ausubel, et al. (1987 and periodic supplements); Deutscher (1990) "Guide to Protein Purification" in *Meth. Enzymol.*, vol. 182, and other volumes in this series; and manufacturer's literature on use of protein purification products, e.g., Pharmacia, Piscataway, N.J., or Bio-Rad, Richmond, Calif.). Combinations with recombinant techniques allow fusion to appropriate segments, e.g., to a FLAG sequence or an equivalent that can be fused via a protease-removable sequence (see, e.g., Hochuli (1990) "Purification of Recombinant Proteins with Metal Chelate Absorbent" in Setlow (ed.) *Genetic Engineering Principle and Methods* 12:87-98, Plenum Press, N.Y.; and Crowe, et al. (1992) *QIAexpress: The High Level Expression & Protein Purification System* QIAGEN, Inc., Chatsworth, Calif.).

Computer sequence analysis is performed, e.g., using available software programs, including those from the GCG (U. Wisconsin) and GenBank sources. Public sequence databases were also used, e.g., from GenBank and others.

II. TSLP Expression in Human Tumor and Normal Cell Line

Human carcinoma cell lines were chosen that were either part of the NCI 60 panel A. Monks et al, J. Natl. Cancer Inst. (1991) 83, 757), or commonly used in the literature. Corresponding normal cell types from each organ or system were obtained from ATCC, Cascade biologics (Portland, Oreg.), or Clonetics (Division of Biowhittaker, Walkersville, Md.). In each case, these were normal, non-transformed, non-immortalized cells, and represent cell types of the particular anatomic region, e.g. fibroblasts, melanocytes and keratinocytes to serve as normal controls for melanoma cell lines, normal mammary epithelial cells to serve as normal controls for breast carcinoma cell lines, etc.

Cells were grown in tissue culture under standard growth conditions, then harvested. Total RNA was isolated using standard guanidium isothocyanate/cesium chloride gradients (Sambrook, J., Fritsch E F, Maniatis T: Molecular Cloning: A Laboratory Manual. New York: Cold Spring Harbor Laboratory Press, 1989). Total RNA was subjected to treatment with DNase to eliminate possible genomic DNA contamination. DNase treated total RNA was reverse transcribed using Superscript II (Gibco/BRL) according to manufacturer's instructions. Primers were designed using Primer Express (PE Biosystems, Foster City, Calif.). Real-time quantitative PCR on 50 ng of cDNA from each sample was performed using Perkin Elmer SYBR green real-time quantitative PCR assay, using an ABI 5700 instrument. Ubiquitin levels were also measured for each sample and used to normalize starting quantities of RNA. The values represent the data normalized to ubiquitin.

III. Analysis of Expression of TSLP mRNA in Transformed Mouse Tumor Cells

The H-Ras transformed mouse keratinocyte cell line PDV and the H-Ras transformed mouse mammary cell line EP2 were treated for 5 days with 5 ng/ml TGFbeta1 (R&D systems) or left untreated. mRNA was prepared using RNeasy columns (Qiagen) (see e.g., Oft et al., (1996) *Genes and Dev.* 10:2462-2477).

B9 squamous carcinoma cells and their derivatives stably overexpressing mutant H-ras and an activated mutant of mSmad2 (see, e.g., Oft et al. (2002) *Nature Cell Biol.* 4:487-494) were cultured to confluence. mRNA was isolated using Qiagen RNAeasy RNA isolation kit. Subsequently the RNA was analyzed by real-time PCR using mTSLP RNA specific primers and normalized to ubiquitin mRNA controls.

IV. TSLP Expression is Lost During Tumor Passage

The Ras transformed Balb/C mouse mammary epithelial cell line, EP2, was injected in nude mice and in syngenic Balb/C mice. Tumor cells were reisolated from the tumor, selected in 0.8 mg/ml G418 (Invitrogen) for four days. mRNA was isolated as described above (see e.g., Oft et al., (1996) *Genes and Dev.* 10:2462-2477).

V. TGFβ Represses TSLP mRNA Expression in Epithelial Tumor Cell Lines

The Ep2 and PDV (DMBA transformed mouse keratinocytes) cell lines were cultured at 60% confluence. Cells were treated with 5 ng/ml TGFβ1 for three consecutive days. The cells were scraped, spun down, and immediately snap frozen in liquid nitrogen. TSLP mRNA was isolated and the expression analyzed by real-time PCR using mTSLP specific RNA primers. Expression levels were normalized to ubiquitin mRNA controls.

VI. TSLP mRNA Expression and Tumor Progression

Ras transformed epithelial cells were subcutaneously injected in syngeneic mice an re-selected after the tumors reached 1 cm³ in volume (see, e.g., Oft et al. (1996) *Genes & Devel.* 10:2462-2477). All cell were cultured to 90% confluence. Cells were scraped, spun down, and immediately snap frozen in liquid nitrogen. mRNA was isolated and subsequently analyzed by real-time PCR. Expression values were normalized to ubiquitin mRNA controls.

VII. Tumor Growth and TSLP mRNA Expression

Tumors were induced on immunocompetent Balb/C mice by subcutaneously injecting 1×10⁶ EPXB tumor cells. The experimental group was subsequently injected with 0.5 mgs of TSLP two times a week following loss of body weight (see e.g., Oft et al., (1996) *Genes and Dev.* 10:2462-2477).

VIII. TSLP mRNA Expression in Carcinogen Treated Mouse Skin

C57B/6/129 mice were treated topically on the back with 50 ug DMBA or 30 ug TPA in 200 ul acetone each, or with acetone alone (control). Small tissue biopsies were harvested from the same mouse at various timepoints (i.e., 0, 5 h, 24 h, 48 h, and 120 h for DMBA; and 0, 5 h, 24 h, and 72 h for TPA). The specimens were immediately snap frozen in liquid nitrogen. Subsequently, mRNA was extracted and analyzed by real-time PCR using mTSLP RNA specific primers and normalized to upbiquitin mRNA controls.

IX. TSLP and Tumor Resistance

Primary NHEK cells (Clonetics, Cambrex) were cultured in defined keratinocyte growth media (Invitrogen) for five passages. The cells were infected at 60% confluency with adenovirus expressing GFP (MOI 100) or left untreated. The cells were scraped, spun down, and immediately snap frozen in liquid nitrogen. Subsequently, the RNA was extracted an analyzed by real time PCR using hTSLP RNA specific primers and normalized to ubiquitin mRNA controls. TSLP mRNA expression showed a significant increase in expression in the adenovirus infected keratinocytes.

To test if the in vitro data above translated into an in vivo setting, 10⁶ Ep-ras cells were injected subcutaneously into syngeneic Balb/C mice. When tumor size reached 200 mm³, adenovirus expressing mTSLP or GFP was injected into the tail vein at 10¹⁰ particles/mouse. Separately, mTSLP protein or PBS (control) was also injected (5 μg 3× per week) into the tail veins at several points from day 1 through day 18. In both, tumor size was measured for 30 days.

X. Listing of Sequence Identifiers

SEQUENCE ID NO: 1 Human TSLP Nucleic Acid sequence.
SEQUENCE ID NO: 2 Human TSLP Amino Acid Sequence
SEQUENCE ID NO: 3 Human IL-7Rα Nucleic Acid Sequence
SEQUENCE ID NO: 4 Human IL-7Rα Amino Acid Sequence
SEQUENCE ID NO: 5 Human TSLPR Nucleic Acid Sequence
SEQUENCE ID NO: 6 Human TSLPR Amino Acid Sequence All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of treating a subject having an epithelial tumor comprising administering to the subject an effective amount of a TSLP protein, wherein the method does not comprise administering to the subject dendritic cells.

2. The method of claim 1, wherein the epithelial tumor is a:
   a) breast tumor;
   b) colon tumor;
   c) lung tumor;
   d) ovary tumor; or
   e) prostate tumor.

* * * * *

SEQUENCE LISTING

<160> NUMBER OF SEQ ID NOS: 6

<210> SEQ ID NO 1
<211> LENGTH: 1419
<212> TYPE: DNA
<213> ORGANISM: Homo sapiens

<400> SEQUENCE: 1

```
ctcgaggcca agaattcggc acgagggcag ccagaaagct ctggagcatc agggagactc      60
caacttaagg caacagcatg ggtgaataag ggcttcctgt ggactggcaa tgagaggcaa     120
aacctggtgc ttgagcactg gcccctaagg caggccttac agatctctta cactcgtggt     180
gggaagagtt tagtgtgaaa ctggggtgga attgggtgtc cacgtatgtt ccctttttgcc    240 ttactatatg ttctgtcagt ttctttcagg aaaatcttca tcttacaact tgtagggctg     300
gtgttaactt acgacttcac taactgtgac tttgagaaga ttaaagcagc ctatctcagt     360
actatttcta aagacctgat tacatatatg agtgggacca aaagtaccga gttcaacaac     420
accgtctctt gtagcaatcg gccacattgc cttactgaaa tccagagcct aaccttcaat     480
cccaccgccg gctgcgcgtc gctcgccaaa gaaatgttcg ccatgaaaac taaggctgcc     540
ttagctatct ggtgccagg ctattcggaa actcagataa atgctactca ggcaatgaag     600
aagaggagaa aaaggaaagt cacaaccaat aaatgtctgg aacaagtgtc acaattacaa     660
```

```
ggattgtggc gtcgcttcaa tcgacccta ctgaaacaac agtaaaccat ctttattatg      720
gtcatatttc acagcaccaa aataaatcat ctttattaag tagatgaaac attaactcta      780
actgtgacaa agaagaccac aaatagttat cttttaatta cagaagagtt tcttaactta      840
cttttgtaag ttttattgt gtaagttat aatgcagggg aagtactact cctcaaatgt        900
tgagggaagc ttccataaca ttgatgactg gcttcatggc agtaattctc ggctgtagtt      960
gcataagcat tgctcaagag gaaaatccaa agtgcagcag gagaactctt ttccctgaaa     1020
aaggaaaaat attgaactca atgatagcac ctaaacttac atttaaaaga cagacattcc     1080
ttctacatgt aatgacactt cttgtgttaa actaaaaatt tacaagagaa gaaagtgaaa     1140
gcaaatgggg tttcacaaat agttgtaaat atagtgaagc aatttgaaat aattttcaag     1200
caaagtattg tgaaagtatt ctaagccaag ttttaaatat tatctaacag acaagagtgg     1260
tatatacaag tagatcctga gaagtacctt tgttacagct actataaata tacatataaa     1320
ttatagaatc tactttaatt tattttgtga acacttttga aaatgtacat gttcctttgt     1380
aattgacact atatatttct taataaaata attctcaaa                            1419
```

```
<210> SEQ ID NO 2
<211> LENGTH: 159
<212> TYPE: PRT
<213> ORGANISM: Homo sapiens

<400> SEQUENCE: 2

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155
```

```
<210> SEQ ID NO 3
<211> LENGTH: 1658
<212> TYPE: DNA
<213> ORGANISM: Homo sapiens

<400> SEQUENCE: 3
ctctctctct atctctctca gaatgacaat tctaggtaca acttttggca tggttttttc       60
tttacttcaa gtcgtttctg gagaaagtgg ctatgctcaa aatggagact ggaagatgc       120 agaactggat gactactcat tctcatgcta tagccagttg gaagtgaatg gatcgcagca     180
```

```
ttcactgacc tgtgcttttg aggacccaga tgtcaacacc accaatctgg aatttgaaat    240
atgtggggcc ctcgtggagg taaagtgcct gaatttcagg aaactacaag agatatattt    300
catcgagaca agaaattcct tactgattgg aaagagcaat atatgtgtga aggttggaga    360
aaagagtcta acctgcaaaa aaatagacct aaccactata gttaaacctg aggctccttt    420
tgacctgagt gtcatctatc gggaaggagc caatgacttt gtggtgacat ttaatacatc    480
acacttgcaa aagaagtatg taaaagtttt aatgcatgat gtagcttacc gccaggaaaa    540
ggatgaaaac aaatggacgc atgtgaattt atccagcaca aagctgacac tcctgcagag    600
aaagctccaa ccggcagcaa tgtatgagat taaagttcga tccatccctg atcactattt    660
taaaggcttc tggagtgaat ggagtccaag ttattacttc agaactccag agatcaataa    720
tagctcaggg gagatggatc ctatcttact aaccatcagc attttgagtt ttttctctgt    780
cgctctgttg gtcatcttgg cctgtgtgtt atggaaaaaa aggattaagc ctatcgtatg    840
gcccagtctc cccgatcata agaagactct ggaacatctt tgtaagaaac caagaaaaaa    900
tttaaatgtg agtttcaatc ctgaaagttt cctggactgc cagattcata gggtggatga    960
cattcaagct agagatgaag tggaaggttt tctgcaagat acgtttcctc agcaactaga   1020
agaatctgag aagcagaggc ttggaggggga tgtgcagagc ccaactgcc catctgagga   1080
tgtagtcgtc actccagaaa gctttggaag agattcatcc ctcacatgcc tggctgggaa   1140
tgtcagtgca tgtgacgccc ctattctctc ctcttccagg tccctagact gcagggagag   1200
tggcaagaat gggcctcatg tgtaccagga cctcctgctt agccttggga ctacaaacag   1260
cacgctgccc cctccatttt ctctccaatc tggaatcctg acattgaacc cagttgctca   1320
gggtcagccc attcttactt ccctgggatc aaatcaagaa gaagcatatg tcaccatgtc   1380
cagcttctac caaaaccagt gaagtgtaag aaacccagac tgaacttacc gtgagcgaca   1440
aagatgattt aaaagggaag tctagagttc ctagtctccc tcacagcaca gagaagacaa   1500
aattagcaaa accccactac acagtctgca agattctgaa acattgcttt gaccactctt   1560
cctgagttca gtggcactca acatgagtca agagcatcct gcttctacca tgtggatttg   1620
gtcacaaggt ttaaggtgac ccaatgattc agctattt                            1658
```

<210> SEQ ID NO 4
<211> LENGTH: 459
<212> TYPE: PRT
<213> ORGANISM: Homo sapiens

<400> SEQUENCE: 4

```
Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110
```

```
Glu Lys Ser Leu Thr Cys Lys Lys Ile Asp Leu Thr Thr Ile Val Lys
            115                 120                 125
Pro Glu Ala Pro Phe Asp Leu Ser Val Ile Tyr Arg Glu Gly Ala Asn
        130                 135                 140
Asp Phe Val Val Thr Phe Asn Thr Ser His Leu Gln Lys Lys Tyr Val
145                 150                 155                 160
Lys Val Leu Met His Asp Val Ala Tyr Arg Gln Lys Asp Glu Asn
                165                 170                 175
Lys Trp Thr His Val Asn Leu Ser Ser Thr Lys Leu Thr Leu Leu Gln
            180                 185                 190
Arg Lys Leu Gln Pro Ala Ala Met Tyr Glu Ile Lys Val Arg Ser Ile
        195                 200                 205
Pro Asp His Tyr Phe Lys Gly Phe Trp Ser Glu Trp Ser Pro Ser Tyr
    210                 215                 220
Tyr Phe Arg Thr Pro Glu Ile Asn Asn Ser Ser Gly Glu Met Asp Pro
225                 230                 235                 240
Ile Leu Leu Thr Ile Ser Ile Leu Ser Phe Phe Ser Val Ala Leu Leu
                245                 250                 255
Val Ile Leu Ala Cys Val Leu Trp Lys Lys Arg Ile Lys Pro Ile Val
            260                 265                 270
Trp Pro Ser Leu Pro Asp His Lys Lys Thr Leu Glu His Leu Cys Lys
        275                 280                 285
Lys Pro Arg Lys Asn Leu Asn Val Ser Phe Asn Pro Glu Ser Phe Leu
    290                 295                 300
Asp Cys Gln Ile His Arg Val Asp Asp Ile Gln Ala Arg Asp Glu Val
305                 310                 315                 320
Glu Gly Phe Leu Gln Asp Thr Phe Pro Gln Gln Leu Glu Glu Ser Glu
                325                 330                 335
Lys Gln Arg Leu Gly Gly Asp Val Gln Ser Pro Asn Cys Pro Ser Glu
            340                 345                 350
Asp Val Val Val Thr Pro Glu Ser Phe Gly Arg Asp Ser Ser Leu Thr
        355                 360                 365
Cys Leu Ala Gly Asn Val Ser Ala Cys Asp Ala Pro Ile Leu Ser Ser
    370                 375                 380
Ser Arg Ser Leu Asp Cys Arg Glu Ser Gly Lys Asn Gly Pro His Val
385                 390                 395                 400
Tyr Gln Asp Leu Leu Leu Ser Leu Gly Thr Thr Asn Ser Thr Leu Pro
                405                 410                 415
Pro Pro Phe Ser Leu Gln Ser Gly Ile Leu Thr Leu Asn Pro Val Ala
            420                 425                 430
Gln Gly Gln Pro Ile Leu Thr Ser Leu Gly Ser Asn Gln Glu Glu Ala
        435                 440                 445
Tyr Val Thr Met Ser Ser Phe Tyr Gln Asn Gln
    450                 455

<210> SEQ ID NO 5
<211> LENGTH: 1557
<212> TYPE: DNA
<213> ORGANISM: Homo sapiens

<400> SEQUENCE: 5
cggcacgagg gcatgggcg gctggttctg ctgtggggag ctgccgtctt tctgctggga      60
ggctggatgg ctttggggca aggaggagca gcagaaggag tacagattca gatcatctac     120
ttcaatttag aaaccgtgca ggtgacatgg aatgccagca atactccag gaccaacctg     180
```

```
actttccact acagattcaa cggtgatgag gcctatgacc agtgcaccaa ctaccttctc      240
caggaaggtc acacttcggg gtgcctccta gacgcagagc agcgagacga cattctctat      300
ttctccatca ggaatgggac gcaccccgtt tcaccgcaa gtcgctggat ggtttattac       360
ctgaaaccca gttccccgaa gcacgtgaga ttttcgtggc atcaggatgc agtgacggtg      420
acgtgttctg acctgtccta cggggatctc ctctatgagg ttcagtaccg gagccccttc      480
gacaccgagt ggcagtccaa acaggaaaat acctgcaacg tcaccataga aggcttggat      540
gccgagaagt gttactcttt ctgggtcagg gtgaaggcta tggaggatgt atatgggcca      600
gacacatacc caagcgactg gtcagaggtg acatgctggc agagaggcga gattcgggat      660
gcctgtgcag agacaccaac gcctcccaaa ccaaagctgt ccaaatttat tttaatttcc      720
agcctggcca tccttctgat ggtgtctctc ctccttctgt ctttatggaa attatggaga      780
gtgaagaagt ttctcattcc cagcgtgcca gacccgaaat ccatcttccc cgggctcttt      840
gagatacacc aagggaactt ccaggagtgg atcacagaca cccagaacgt ggcccacctc      900
cacaagatgg caggtgcaga gcaagaaagt ggccccgagg agcccctggt agtccagttg      960
gccaagactg aagccgagtc tcccaggatg ctggacccac agaccgagga gaaagaggcc     1020
tctgggggat ccctccagct tccccaccag cccctccaag gcggtgatgt ggtcacaatc     1080
gggggcttca cctttgtgat gaatgaccgc tcctacgtgg cgttgtgatg acacaccac     1140 tgtcaaagtc aacgtcagga tccacgttga catttaaaga cagagggac tgtcccgggg     1200 actccacacc accatggatg ggaagtctcc acgccaatga tggtaggact aggagactct     1260
gaagacccag cctcaccgcc taatgcggcc actgccctgc taactttccc ccacatgagt     1320
ctctgtgttc aaaggcttga tggcagatgg gagccaattg ctccaggaga tttactccca     1380
gttccttttc gtgcctgaac gttgtcacat aaaccccaag gcagcacgtc caaaatgctg     1440
taaaaccatc ttcccactct gtgagtcccc agttccgtcc atgtacctgt tccatagcat     1500
tggattctcg gaggattttt tgtctgtttt gagactccaa accacctcta cccctac        1557
```

<210> SEQ ID NO 6
<211> LENGTH: 371
<212> TYPE: PRT
<213> ORGANISM: Homo sapiens

<400> SEQUENCE: 6

```
Met Gly Arg Leu Val Leu Leu Trp Gly Ala Ala Val Phe Leu Leu Gly
1               5                   10                  15

Gly Trp Met Ala Leu Gly Gln Gly Gly Ala Ala Glu Gly Val Gln Ile
            20                  25                  30

Gln Ile Ile Tyr Phe Asn Leu Glu Thr Val Gln Val Thr Trp Asn Ala
        35                  40                  45

Ser Lys Tyr Ser Arg Thr Asn Leu Thr Phe His Tyr Arg Phe Asn Gly
    50                  55                  60

Asp Glu Ala Tyr Asp Gln Cys Thr Asn Tyr Leu Leu Gln Glu Gly His
65                  70                  75                  80

Thr Ser Gly Cys Leu Leu Asp Ala Glu Gln Arg Asp Asp Ile Leu Tyr
                85                  90                  95

Phe Ser Ile Arg Asn Gly Thr His Pro Val Phe Thr Ala Ser Arg Trp
            100                 105                 110

Met Val Tyr Tyr Leu Lys Pro Ser Pro Lys His Val Arg Phe Ser
        115                 120                 125
```

```
Trp His Gln Asp Ala Val Thr Val Thr Cys Ser Asp Leu Ser Tyr Gly
    130                 135                 140
Asp Leu Leu Tyr Glu Val Gln Tyr Arg Ser Pro Phe Asp Thr Glu Trp
145                 150                 155                 160
Gln Ser Lys Gln Glu Asn Thr Cys Asn Val Thr Ile Glu Gly Leu Asp
                165                 170                 175
Ala Glu Lys Cys Tyr Ser Phe Trp Val Arg Val Lys Ala Met Glu Asp
                180                 185                 190
Val Tyr Gly Pro Asp Thr Tyr Pro Ser Asp Trp Ser Glu Val Thr Cys
            195                 200                 205
Trp Gln Arg Gly Glu Ile Arg Asp Ala Cys Ala Glu Thr Pro Thr Pro
    210                 215                 220
Pro Lys Pro Lys Leu Ser Lys Phe Ile Leu Ile Ser Ser Leu Ala Ile
225                 230                 235                 240
Leu Leu Met Val Ser Leu Leu Leu Leu Ser Leu Trp Lys Leu Trp Arg
                245                 250                 255
Val Lys Lys Phe Leu Ile Pro Ser Val Pro Asp Pro Lys Ser Ile Phe
                260                 265                 270
Pro Gly Leu Phe Glu Ile His Gln Gly Asn Phe Gln Glu Trp Ile Thr
            275                 280                 285
Asp Thr Gln Asn Val Ala His Leu His Lys Met Ala Gly Ala Glu Gln
    290                 295                 300
Glu Ser Gly Pro Glu Glu Pro Leu Val Val Gln Leu Ala Lys Thr Glu
305                 310                 315                 320
Ala Glu Ser Pro Arg Met Leu Asp Pro Gln Thr Glu Glu Lys Glu Ala
                325                 330                 335
Ser Gly Gly Ser Leu Gln Leu Pro His Gln Pro Leu Gln Gly Gly Asp
                340                 345                 350
Val Val Thr Ile Gly Gly Phe Thr Phe Val Met Asn Asp Arg Ser Tyr
            355                 360                 365
Val Ala Leu
    370
```